United States Patent [19]
Berelsman et al.

[11] Patent Number: 5,827,311
[45] Date of Patent: Oct. 27, 1998

[54] CARPAL TUNNEL TOME

[75] Inventors: Brian K. Berelsman, Bourbon; Daniel E. Williamson, Warsaw, both of Ind.

[73] Assignee: Biomet Inc, Warsaw, Ind.

[21] Appl. No.: 852,995

[22] Filed: May 8, 1997

[51] Int. Cl.$^6$ .................................................. A61B 17/32
[52] U.S. Cl. ........................................... 606/167; 30/294
[58] Field of Search ............................... 606/1, 166, 167, 606/170; 30/289, 294

[56] References Cited

U.S. PATENT DOCUMENTS

| | | |
|---|---|---|
| 117,588 | 8/1871 | Woods . |
| 2,764,814 | 10/1956 | Jecker . |
| 3,336,927 | 8/1967 | Klebanoff . |
| 3,365,798 | 1/1968 | Cunningham . |
| 3,751,806 | 8/1973 | Patrick . |
| 3,831,274 | 8/1974 | Horrocks . |
| 3,972,117 | 8/1976 | Fogg . |
| 3,975,822 | 8/1976 | Mabus . |
| 4,026,295 | 5/1977 | Lieberman . |
| 4,432,138 | 2/1984 | Piccolo, Jr. . |
| 4,962,770 | 10/1990 | Agee et al. . |
| 5,029,573 | 7/1991 | Chow . |
| 5,089,000 | 2/1992 | Agee et al. . |
| 5,122,152 | 6/1992 | Mull ...................................... 606/170 |
| 5,253,659 | 10/1993 | Mc Namara et al. . |
| 5,269,796 | 12/1993 | Miller et al. . |
| 5,273,024 | 12/1993 | Memon et al. . |
| 5,323,765 | 6/1994 | Brown . |
| 5,325,883 | 7/1994 | Orr . |
| 5,334,214 | 8/1994 | Putman . |
| 5,341,822 | 8/1994 | Farr et al. . |
| 5,353,812 | 10/1994 | Chow . |
| 5,387,222 | 2/1995 | Strickland . |
| 5,507,800 | 4/1996 | Strickland . |

FOREIGN PATENT DOCUMENTS

| | | |
|---|---|---|
| 3826786 | 8/1990 | Germany . |
| 906543 | 2/1982 | U.S.S.R. . |
| 1165373 | 7/1985 | U.S.S.R. . |
| 154416A | 1/1989 | U.S.S.R. . |
| 1561965 | 5/1990 | U.S.S.R. . |
| 12354 | 7/1891 | United Kingdom . |
| 2203341 | 4/1987 | United Kingdom . |
| WO 9301275 A1 | 7/1993 | WIPO . |

OTHER PUBLICATIONS

David M. Pagnanelli, M.D. et al "Carpal Tunnel Release at One Operation: Report of 228 Patients," *Neurosurgery* vol. 31 No. 6 Dec. 1992.
David M. Pagnanelli, M.D. et al "Carpal Tunnel Syndrone: Surgical Treatment Using the Paine Retinaculatome," *J. Neurosurgery* vol.75, No.6 Jul. 1991.
Lee et al "Carpal Tunnel Release with a Small Palmar Incision" *Hand Clinics* vol. 12 No. May 1996 pp. 271–284.
Biomet Inc. Catalog "Minimally Open Technique" 1996.
Stryker Instruments Corp. Catalog "Knife Light" 1997.
Kenneth W. E. Paine, MD et al., "Decompression Using the Paine Retinaculotome," *J. Neurosurgery* vol. 59, Dec. 1983.
Ruggeles Corporation Catalog, R–520 Paine's Carpal Tunnel Retinaculotome, p. 59.

*Primary Examiner*—William Lewis
*Attorney, Agent, or Firm*—Ernest E. Helms

[57] ABSTRACT

A two piece construction disposable carpal tunnel ligament tome is provided. In a preferred embodiment the tome has a handle, stem, cutting head with two forward extending and parallel spaced upper and lower forks. The handle, stem, cutting head and forks are injection molded as one plastic piece. Mounted in the cutting head is a blade fabricated from flat stock metal with a forward facing cutting edge concealed by the forks. Extending forward from the blade are upper and lower fork reinforcement members. The fork reinforcements are encapsulated by the molded upper and lower forks. The inventive carpal tunnel ligament tome provides very rigid forks, yet does not require the extensive machining required by tomes with metal forks. Since the blade and fork reinforcement can be fabricated from a flat stock material, fabrication costs can be lowered with extremely high performance of the tome being maintained.

20 Claims, 2 Drawing Sheets

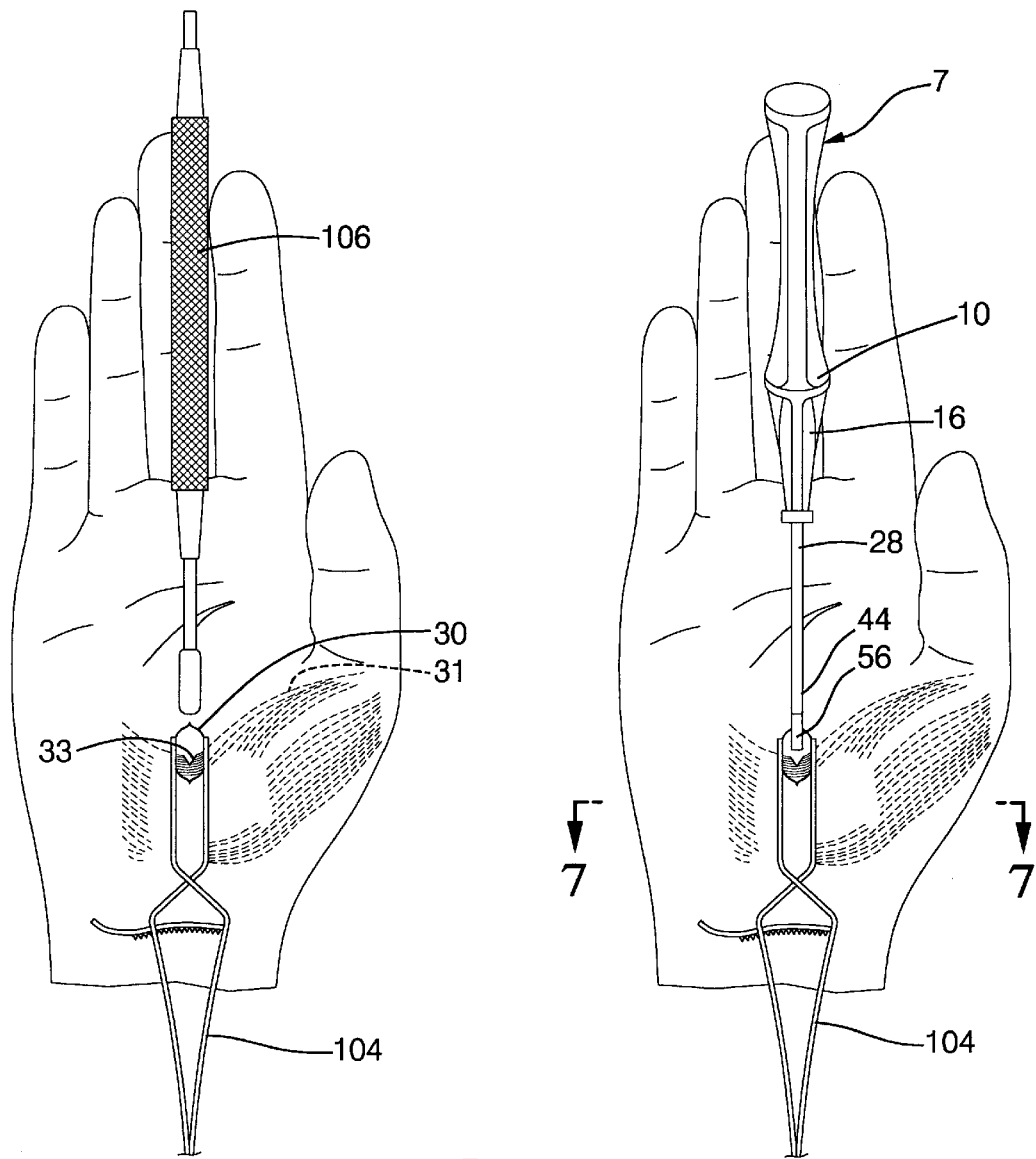
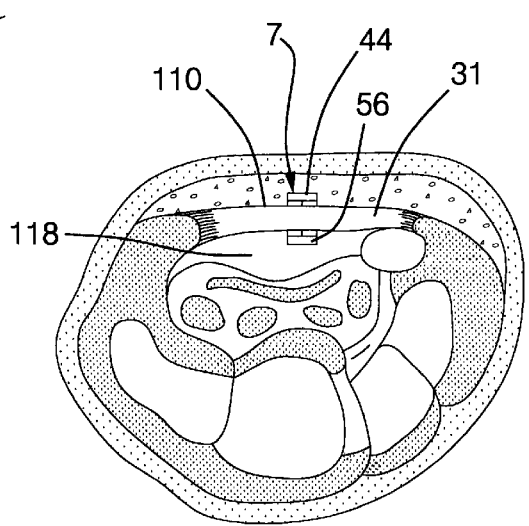
FIG. 5  FIG. 6
FIG. 7

CARPAL TUNNEL TOME

BACKGROUND OF THE INVENTION

The present invention relates generally to surgical instruments and in particular relates to a tome for dividing the transverse carpal ligament.

Carpal tunnel syndrome (CTS) is the most common peripheral nerve entrapment neuropathy and the most common cause of paresthesias in the first three fingers and of nocturnal paresthesias. CTS often occurs in individuals whose occupations expose them to vibrating tools or repetitive hand motions. Although CTS was recognized as nerve compression over 140 years ago, surgical treatment was not discussed until 80 years later.

Currently many carpal tunnel syndrome patients are surgically treated by dividing patient's transverse carpal ligament to relieve pressure on the patient's median nerve. The above noted procedure typically requires the making of an incision in the palm, sometimes extending across the wrist, directly above the carpal ligament to divide the deep transverse carpal ligament. The above noted procedure has been successful in treating many CTS patients, however it is often accompanied by tenderness about the incision site in the proximal palm and across the wrist. In addition, patients frequently experience "pillar pain" at the base of the thenar, and hypothenar eminences, just distal to the wrist crease and on each side of the surgical scar. The post-surgical discomfort has been implicated as the cause for the slow return of patients to occupational activities following conventional carpal tunnel release surgery.

Efforts have been made to alter the technique of carpal tunnel release surgery to minimize the amount of proximal palm and pillar pain, and to allow patients to resume normal activities more quickly. One such method involves making a relatively shorter incision located entirely in the palm and then dividing the deep transverse carpal ligament by straddling the ligament with small blunt scissors that are passed proximally toward the patient's wrist. Although the "scissors" technique is effective, there is some danger of inadvertent injury to the median nerve or other structures from the tip of the scissors as they are blindly passed in a proximal direction. Further, the length of incision required to divide the majority of the ligament prior to scissors passage may still be large enough to lead to some palmar pain.

The use of one of several endoscopic methods for division of the deep transverse carpal ligament has also received considerable popularity in the past several years. Endoscopic techniques employ the passage of a special instrument beneath the carpal ligament such as for example, the method shown in Chow U.S. Pat. No. 5,029,573. Fiber optics and special cutting instruments are then utilized to observe and divide the ligament. Although efforts have been made to make endoscopic techniques as simple and safe as possible, they still require specialized training and a reasonably long learning curve before the surgeon becomes adept at their use. Complications such as injury to or division of the median nerve, one of its branches, the tendons within the carpal vault or the superficial arterial arch of the palm have been described with disconcerting frequency. Endoscopic techniques also tend to take up a relatively large amount of surgical time.

Strickland U.S. Pat. Nos. 5,387,222 and 5,507,800 provides a surgical technique that only requires a small midpalmar incision and utilizes a small cutting instrument referred to as a tome to protect adjacent tissues when cutting the ligament. The Strickland tome has a rear handle and a blade that is mounted on a front end cutting head. The blade has a forward directed cutting edge. The blade is concealed between upper and lower forward extending forks (sometimes referred to as protuberances or skids) which are connected to the cutting head. The upper fork is shorter than the lower fork to allow the surgeon to better visualize the tome straddling the carpal ligament when inserted.

To help control and or lower medical costs, and to ensure the quality and sterilization of a surgical instrument used on a patient, many surgical instruments are being fabricated to be disposable. An embodiment of Strickland provides a two piece construction disposable tome. The Strickland disposable tome has a plastic handle, stem, and partial cutting head. The partial cutting head also includes an upper fork. The second portion of the instrument includes a metal blade and lower fork. The blade requires a high degree of machining to form its surgical quality cutting edge. Additionally the lower fork must be carefully machined to establish a smooth peripheral surface which will not cause injury when used in the surgical procedure. The two machining requirements on a common metal piece significantly contribute to the cost of the tome. The divergent transverse dimensional requirements of the blade and the lower fork require that the blade be fabricated from a piece of metal that is at least as thick as the lower fork, thereby significantly adding to material cost of the blade. It would be highly desirable to provide a tome that can be made as reliable as the tome disclosed in Strickland and yet at the same time be inexpensive to fabricate.

SUMMARY OF THE INVENTION

The present invention in a preferred embodiment provides a two piece construction disposable carpal tunnel ligament tome. In a preferred embodiment the inventive tome has a handle, stem, cutting head with two forward extending and parallel spaced upper and lower forks. The handle, stem, cutting head and forks are injection molded as one plastic piece. Mounted in the cutting head is a blade fabricated from flat stock metal with a forward facing cutting edge concealed by the forks. Extending forward from the blade are upper and lower fork reinforcement members. The fork reinforcements are encapsulated by the molded upper and lower forks. The inventive carpal tunnel ligament tome provides very rigid forks, yet does not require the extensive machining required by tomes with metal forks. Since the blade and fork reinforcements can be fabricated from a flat stock material, fabrication costs can be lowered with extremely high performance of the tome being maintained.

BRIEF DESCRIPTION OF THE DRAWINGS

FIG. 5 is a view of a palmar side of a patient's hand showing the use of an elevator to prepare the patients palm for later insertion of the tome as shown in FIG. 1.

FIG. 6 is a view of a palmar side of a patient's hand showing the use of the carpal tunnel ligament tome as shown in FIG. 1.

FIG. 7 is a cross sectional view through a patient's wrist at a midpoint in the surgery taken along line 7—7 of FIG. 6.

DETAILED DESCRIPTION OF THE PREFERRED EMBODIMENT

Figure 1:
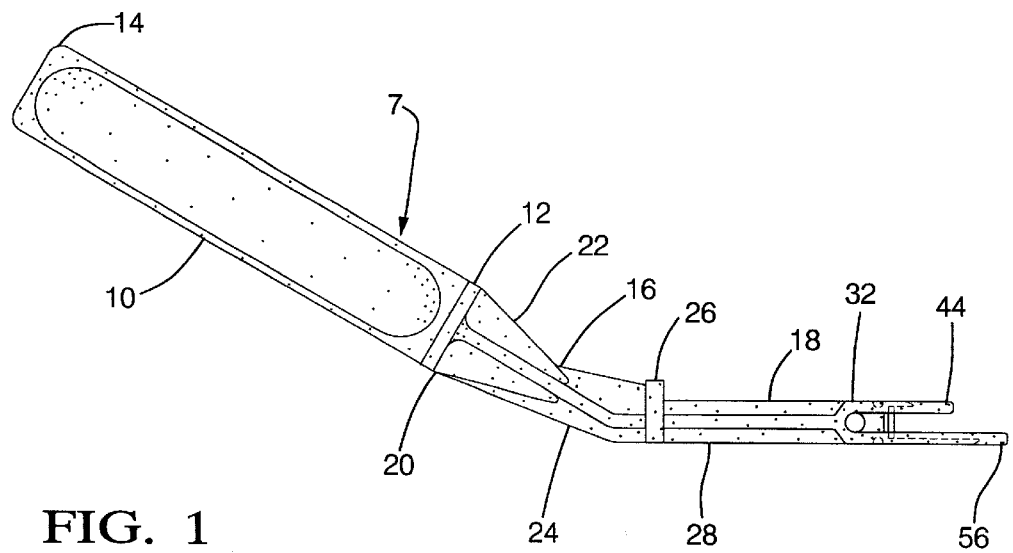
FIG. 1 is a side elevation view of a preferred embodiment carpal tunnel ligament tome according to the present invention.
Figure 2:
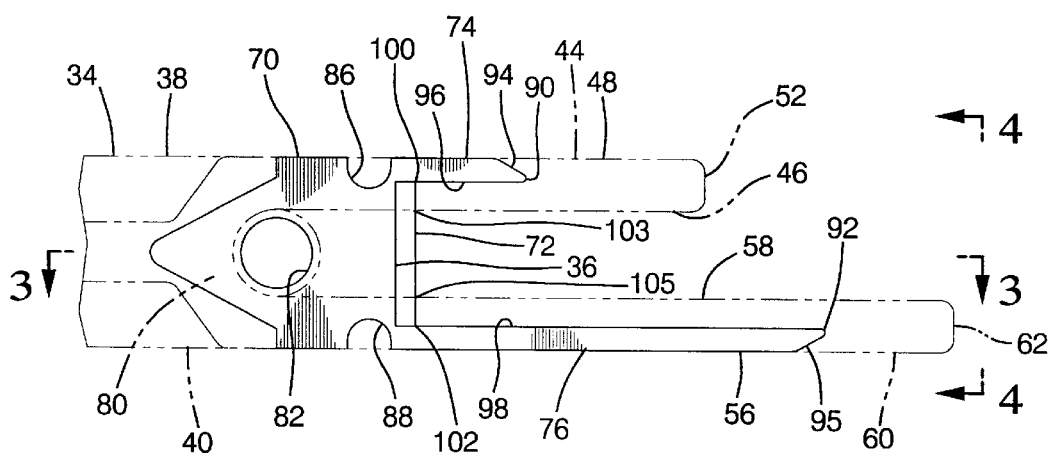
FIG. 2. is an enlarged side elevation view of a blade and integral fork reinforcements of the carpal tunnel ligament tome shown in FIG. 1 with portions of a cutting head shown in phantom.
Figure 3:
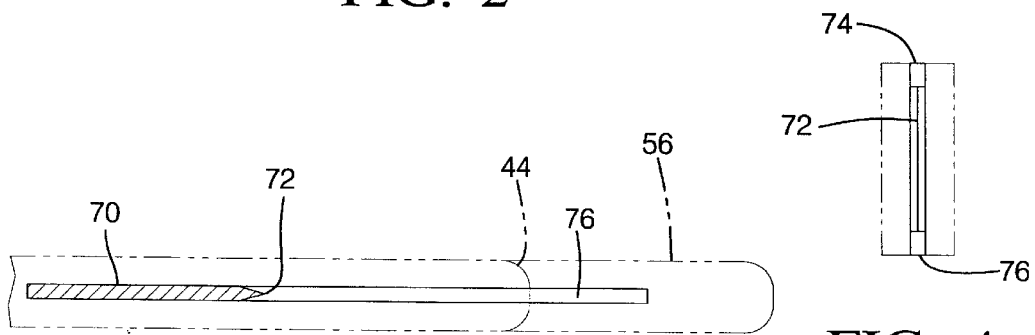
FIG. 3 is a view taken along line 3—3 of FIG. 2.
Figure 4:
FIG. 4 is a view taken along line 4—4 of FIG. 2.

Referring now to the FIGS. 1–4, a preferred embodiment carpal tunnel ligament tome 7 according to the present invention has a handle 10. The handle 10 has a front end 12 and a rear end 14. The handle IO can be a metal or a polymeric material such as a moldable plastic. As shown the handle 10 is formed from an injection molded acrylonitrile butadiene styrene (ABS) plastic.

Integrally connected with the handle IO is a stem 16. The stem 16 has a front end 18 and a rear end 20. The rear end 20 of the stem is connected with the handle front end 12. The stem 16 includes a rear section 22, a midsection 24, a flange bumper or stop 26 and an elongated section 28. The elongated section 28 is angled with respect to the handle 10. The angle of the elongated section 28 is provided to facilitate the approach and entry into the small wound 30 (FIG. 5) used to identify and divide the transverse carpal ligament 31. The triangular shaped bumper 26 is used to prevent a surgeon from proceeding too far into the wound with the tome 7. In an alternative embodiment (not shown) the stem is just a linear extension of the handle.

Forward of the stem 16 is a cutting head 32. The cutting head 32 has a rear end 34 and an opposite front end 36. The stem rear end 34 is integrally connected to the stem elongated section 28 front end 18. The cutting head has an upper first side 38 and a lower second side 40.

A forward extending first fork 44 is integrally connected to the front end 36 of the cutting head. The first fork 44 is molded to have smooth generally flat inner and outer surfaces 46, 48. The outer surface 48 is generally continuous to the cutting head first side 38. The first fork 44 has a cross sectional dimension of approximately 1.5 by 5 mm. The first fork 44 extends forward from the cutting head front end 36 approximately 8 mm. and at its extreme end 52 is generally rounded to provide a blunt tip. Bluntness at the extreme end 52 is desired to prevent inadvertent entanglement or injury to tissue surrounding the carpal ligament 31.

Parallel spaced from the first fork 44 is a second fork 56. The forward extending second fork 56 is also integrally connected to the front end 36 of the cutting head. The second fork 56 is molded to have smooth generally flat inner and outer surfaces 58, 60. The outer surface 60 is generally continuous to the cutting head second side 40. The second fork 56 has a cross sectional dimension of approximately 1.5 by 5 mm. The second fork 56 extends approximately 9 mm. beyond the first fork 44. The second fork 56 has a generally rounded blunted extreme end 62. If desired the extreme end 62 may be modified as described in Strickland U.S. Pat. No. 5,507,800, the disclosure of which is incorporated by reference herein.

Mounted in the cutting head 32 is a blade 70. The blade 70 has a forward directed generally perpendicular cutting edge 72 concealed by a narrow passage between the two forks 44, 56.

The blade can be fabricated from a flat stock metal such as stainless steel and as shown is approximately 0.5 mm. thick. Integrally connected with the blade 70 are forward extending parallel spaced first and second fork reinforcement members 74, 76. The first fork reinforcement 74 has a vertical thickness of approximately 0.75 mm. thickness and the second fork reinforcement 76 has a vertical thickness that is about 0.25 mm. greater than that of the first fork reinforcement. Typically the ratio of length of the second fork reinforcement 76 to the first fork reinforcement will be at least 3:1.

The blade 70 and fork reinforcements 74, 76 are connected by encapsulation in the cutting head 32 and forks 44, 56 during the injection molding of the cutting head 32 and forks 44, 56. To stabilize the blade 70 during molding there is provided a tail 80 and a mold pin locator opening 82. The blade 70 has upper and lower surfaces optionally generally flush with the first and second sides 38, 40 of the cutting head. Located rearward of the cutting edge 72, along the blade upper and lower surfaces are indentations 86, 88 to aid in locking the blade 70 to the cutting head 32. The fork reinforcements 74, 76 have extreme ends 90, 92 that are tapered outward at an angle of approximately 30 degrees. The aforementioned tapers provides angled surfaces 94, 95 for the forks 44, 56 to push against. When the tome 7 is in the process of cutting the ligament 31 the angled surfaces 94, 95 help to prevent the forks 44, 56 from separating from their respective reinforcements 74,76.

Due to machining constraints, a slight radius is formed at the intersections 100, 102 of the cutting edge 72 and inner surfaces 96, 98 of the fork reinforcements. Therefore the sharpness of the cutting edge 62 is limited at the cutting edge intersections 100, 102. To ensure that a patient's carpal ligament 31 is only exposed to a portion of the cutting edge 72 with maximum sharpness, the intersections 103 and 105 of the fork inner surfaces 46, 58 with the cutting edge 72 are inboard of the intersections 100, 102. Therefore it is preferable that the fork inner surfaces 46, 58 traverse over their respective fork reinforcements inner surfaces 96, 98. The outer surfaces of the reinforcements 74,76 are optionally flush with the fork outer surfaces 48, 60.

Operative Procedure

A local anesthesia is administered to the patient under the proximal palmar skin, across the wrist crease and into the sub facial wrist compartment and into the carpal tunnel. Under tourniquet hemostasis, a single 2.0 cm. longitudinal palmar incision is made using landmarks which identify the distal border of the transverse carpal ligament. The aforementioned incision forms the wound 30 (FIG. 5).

A Holzheimer self-retaining retractor 104 is utilized to hold the wound 30 open. Under direct visualization, a scalpel is used to make a 1.0 cm. incision 33 in a distal portion of the carpal ligament 31. The contents of the carpal vault 118 (FIG. 7) are then exposed. Direct viewing of the median nerve and the superficial palmar arch safely protects these structures from injury during the remainder of the operative procedure.

A blunt pilot or Freer elevator 106 (FIG. 5) is then placed underneath the partially divided carpal ligament 31 and passed proximally toward the patient's wrist to separate the contents of the carpal tunnel from the carpal ligament 31. The blunt pilot is removed.

A palmar stripper (not shown) is inserted into the carpal ligament incision 33. The palmar stripper is an instrument shaped similar to the tome 7 which does not have a cutting edge on its head. However the palmar stripper has a sharpened upper fork (commonly referred to as a skid). A blunt lower fork of the palmar stripper glides underneath the carpal ligament allowing the upper fork to pass palmar to the ligament. The aforementioned movement of the palmar stripper creates a channel though the dense tissue connecting the palmar fascia to the distal portion of the carpal ligament. The palmar stripper will stop when its head (commonly referred to as a post) touches an edge of the carpal ligament incision 33. The palmar stripper is then removed.

A double pilot (not shown) is then introduced into the carpal ligament incision 33. The double pilot is an instrument shaped similar to the tome 7. However the double pilot does not have a cutting edge on its head. The double pilot has blunt upper and lower forks which are longer than the upper and lower forks of the tome 7. The upper and lower forks of the double pilot straddle the carpal ligament 31. The double pilot is pushed proximally until its head is stopped by the edge of the carpal ligament incision 33. A pathway is now established for the tome 7. The double pilot is removed.

The tome 7 in placed into the carpal ligament incision 33. The second fork 56 is placed underneath the carpal ligament 31. The first fork 44 is then placed over the carpal ligament 31. The surgeon will move the tome 7 through the established pathway proximally toward the patients wrist to completely divide the carpal ligament 31. An optional tome guide (not shown) can be inserted between the under surface of the carpal ligament 31 and the contents of the carpal vault 118 prior to insertion of the tome 7. The guide provides a channel that further controls the path of the tome 7 during ligament division.

The triangular bumper 26 prevents the tome 7 from passing to far proximally. The tome 7 should not be reintroduced into the wound made into the carpal ligament for a second pass.

A more detailed understanding of some of the surgical instruments herein described other the tome 7 may be acquired by a review of Strickland U.S. Pat. 5,387,722, and 5,507,800 the disclosures of which are incorporated by reference herein and Lee MD, Plancher MD, & Strickland MD "Carpal Tunnel Release With A Small Palmar Incision" Hand Clinics Volume 12 Number 2 May 1996.

In accordance with the provisions of the patent statutes, the principle and mode of operation of this invention have been explained and illustrated in its preferred embodiment. However, it must be understood that this invention may be practiced otherwise than as specifically explained and illustrated without departing from its spirit or scope.

What is claimed is:

1. A carpal tunnel tome comprising:
   a stem having a front end and a rear end;
   a cutting head having a front end and a rear end, the rear end of the cutting head being connected to the front end of the stem, the cutting head having a first side and a second side;
   a polymeric first fork connected to the cutting head along the front end of the cutting head and extending generally forward from the cutting head, the first fork being generally continuous to the first side of the cutting head;
   a polymeric second fork connected to the cutting head along the front end of the cutting head and extending generally forward from the cutting head parallel spaced from the first fork, the second fork being generally continuous to the second side of the cutting head;
   a blade, mounted to the cutting head between the two forks with a forward directed cutting edge;
   a first fork reinforcement member having a stiffness greater than a stiffness of the first fork, the first fork reinforcement member being connected with the first fork; and
   a second fork reinforcement member having a stiffness greater than the stiffness of the second fork, the second fork reinforcement member being connected with the second fork.

2. A carpal tunnel tome as described in claim 1 wherein at least one of the forks is fabricated from a moldable plastic material.

3. A carpal tunnel tome as described in claim 1 wherein the forks are formed integral with the cutting head.

4. A carpal tunnel tome as described in claim 3 wherein the stem and cutting head are formed integrally.

5. A carpal tunnel tome as described in claim 1 wherein the second fork extends a greater distance from the cutting head than the first fork.

6. A carpal tunnel tome as described in claim 1 wherein the fork reinforcements are integrally connected with the blade.

7. A carpal tunnel tome as described in claim 6 wherein the fork reinforcements and blade are formed from a flat stock of metallic material.

8. A carpal tunnel tome as described in claim 1 wherein at least one of the forks encapsulates its reinforcement member.

9. A carpal tunnel tome as described in claim 1 wherein the second fork reinforcement member has a greater vertical thickness than the first fork reinforcement member.

10. A carpal tunnel tome as described in claim 1 wherein the second reinforcement member is longer than the first fork.

11. A carpal tunnel tome as described in claim 1 wherein at least one of the fork reinforcements has a tapered edge at its forward end.

12. A carpal tunnel tome as described in claim 11 wherein the fork reinforcement end is tapered outwardly.

13. A carpal tunnel tome as described in claim 1 wherein a handle is connected with the stem.

14. A carpal tunnel tome as described in claim 1 wherein the blade along an outer edge has an indentation for locking into the cutting head.

15. A carpal tunnel tome as described in claim 14 wherein the indentation is rearward of the cutting edge.

16. A carpal tunnel tome as described in claim 1 wherein an intersection of the fork with the cutting edge is inboard of an intersection of the respective fork reinforcement with the cutting edge.

17. A carpal tunnel tome as described in claim 16 wherein the cutting edge is generally perpendicular to the first and second forks.

18. A carpal tunnel tome comprising:
   a handle having a front end and a rear end;
   a stem having a front end and a rear end, the rear end of the stem being connected with the front end of the handle;
   a cutting head having a front end and a rear end, the rear end of the cutting head being connected to the front end of the stem, the cutting head having a first side and a second side;
   a polymeric first fork connected to the cutting head along the front end of the cutting head and extending generally forward from the cutting head, the first fork including a generally flat outer surface continuous to the first side of the cutting head;
   a polymeric second fork connected to the cutting head along the front end of the cutting head and extending generally forward from the cutting head parallel spaced from the first fork, the second fork including a generally flat outer surface continuous to the second side of the cutting head;
   a blade, mounted to the cutting head between the two forks with a forward directed cutting edge;

a first fork reinforcement member having a stiffness greater than a stiffness of the first fork, the first fork reinforcement member being connected with the first fork; and a second fork reinforcement member having a stiffness greater than the stiffness of the second fork, the second fork reinforcement member being connected with the second fork.

19. A carpal tunnel tome as described in claim 18 wherein the fork reinforcements and blade are formed from a flat stock of metallic material and the forks encapsulate their respective reinforcement member.

20. A carpal tunnel tome comprising:

a molded plastic handle having a front end and a rear end;

a stem angled from the handle having a front end and a rear end, the rear end of the stem being integrally connected with the front end of the handle;

a cutting head having a front end and a rear end, the rear end of the cutting head being integrally connected to the front end of the stem, the cutting head having a first side and a second side;

a first fork integrally connected to the cutting head along the front end of the cutting head and extending generally forward from the cutting head, the first fork including a generally flat outer surface continuous to the first side of the cutting head;

a second fork integrally connected to the cutting head along the front end of the cutting head and extending generally forward from the cutting head parallel spaced from the first fork, the second fork including a generally flat outer surface continuous to the second side of the cutting head;

a metal blade fabricated from a flat stock, mounted to the cutting head between the two forks with a forward directed cutting edge;

a first fork reinforcement member integrally connected with the blade and extending forward from the blade, the first fork reinforcement member being encapsulated by the first fork; and a second fork reinforcement member integrally connected with the blade and extending forward from the blade, the second fork reinforcement member having a length at least 3 times as great as a length of the first reinforcement member, the second fork reinforcement member being encapsulated by the second fork.

* * * * *